US012376841B2

United States Patent
Masgnaux et al.

(10) Patent No.: US 12,376,841 B2
(45) Date of Patent: Aug. 5, 2025

(54) ADJUSTABLE ENDOSCOPIC TRACTION DEVICE

(71) Applicants: HOSPICES CIVILS DE LYON, Lyons (FR); UNIVERSITE CLAUDE BERNARD LYON 1, Villeurbanne (FR); A-TRACT DEVICE & CO, Belmont d'Azergues (FR)

(72) Inventors: Louis-Jean Masgnaux, Lyons (FR); Jean Grimaldi, Lyons (FR); Soline Brun, Lyons (FR); Mathieu Pioche, Belmont-d'Azergues (FR); Jérôme Rivory, Vourles (FR)

(73) Assignees: HOSPICES CIVILS DE LYON, Lyons (FR); UNIVERSITE CLAUDE BERNARD LYON 1, Villeurbanne (FR); A-TRACT DEVICE & CO, Belmont d'Azergues (FR)

( * ) Notice: Subject to any disclaimer, the term of this patent is extended or adjusted under 35 U.S.C. 154(b) by 0 days.

(21) Appl. No.: 18/858,542

(22) PCT Filed: Apr. 25, 2023

(86) PCT No.: PCT/EP2023/060803
§ 371 (c)(1),
(2) Date: Oct. 21, 2024

(87) PCT Pub. No.: WO2023/208930
PCT Pub. Date: Nov. 2, 2023

(65) Prior Publication Data
US 2025/0107792 A1    Apr. 3, 2025

(30) Foreign Application Priority Data
Apr. 26, 2022 (FR) ........................ 2203841

(51) Int. Cl.
A61B 17/02       (2006.01)
A61B 17/00       (2006.01)
(Continued)

(52) U.S. Cl.
CPC .. *A61B 17/0218* (2013.01); *A61B 17/320016* (2013.01); *A61B 2017/00269* (2013.01)

(58) Field of Classification Search
CPC ........ A61B 17/0218; A61B 17/320016; A61B 2017/00269
See application file for complete search history.

(56) References Cited

U.S. PATENT DOCUMENTS

2021/0169464 A1*   6/2021   Lee ................... A61B 17/10

FOREIGN PATENT DOCUMENTS

| WO | 2020018566 A1 | 1/2020 |
| WO | 2021009835 A1 | 1/2021 |
| WO | 2022015931 A1 | 1/2022 |

OTHER PUBLICATIONS

WIPO/ISA/EPO, International Search Report and Written Opinion issued in corresponding International Application No. PCT/EP2023/060803 on Jul. 13, 2023, 11 pages.

* cited by examiner

*Primary Examiner* — Scott Luan
(74) *Attorney, Agent, or Firm* — J. Peter Paredes; Amin Wasserman Gurnani LLP

(57) ABSTRACT

The aim of the invention is to provide a traction device for sufficiently exposing the submucosa so as to provide suitable conditions for the dissection device to move freely throughout the entire dissection of the tumoral mucosa. The traction device (1) of the invention is characterised in that it comprises a proximal anchor (3) that is mounted so as to move relative to an elastic member (2) between a minimum proximal distance and a maximum proximal distance, and in (Continued)

that the traction device comprises an adjustment member (6) configured to adjust the maximum proximal distance between the initial maximum proximal distance and a final maximum proximal distance smaller than the initial maximum proximal distance.

10 Claims, 5 Drawing Sheets

(51) Int. Cl.
*A61B 17/04* (2006.01)
*A61B 17/08* (2006.01)
*A61B 17/32* (2006.01)
*A61B 90/00* (2016.01)

[Fig.1]
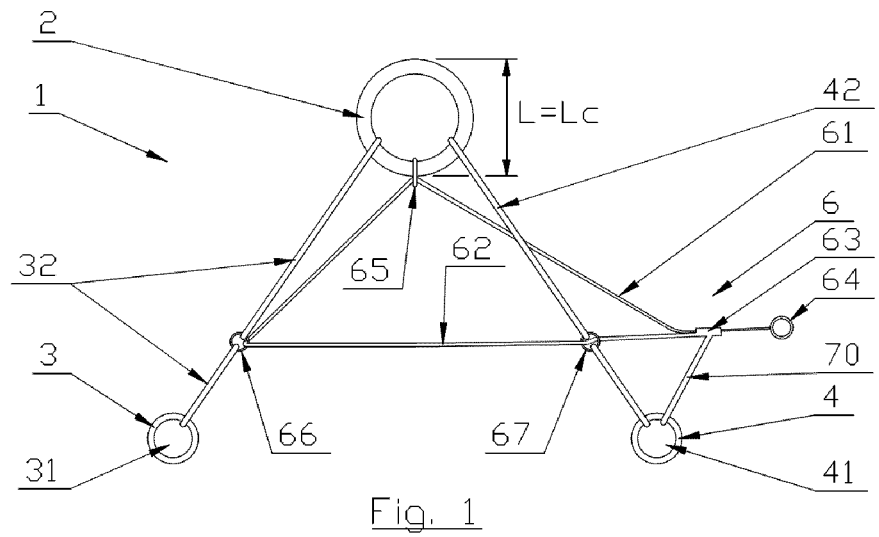
[Fig.2]
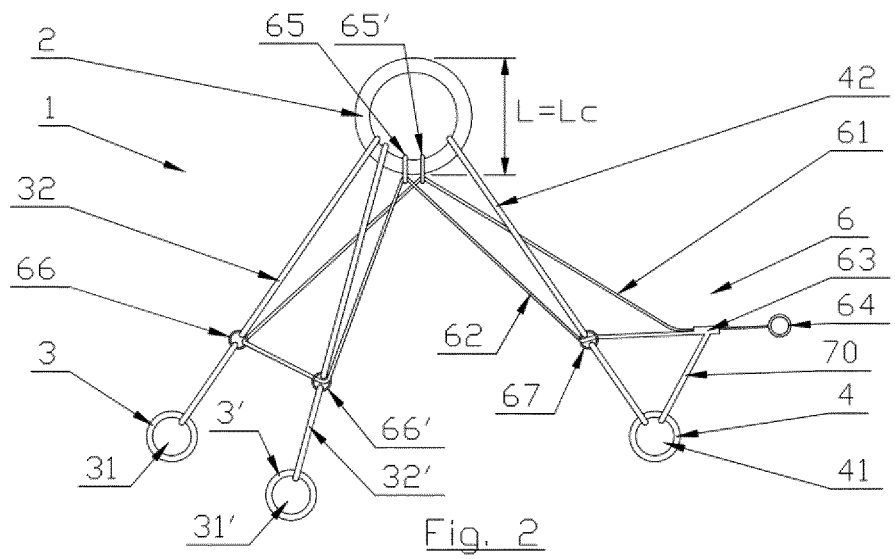

[Fig.7]
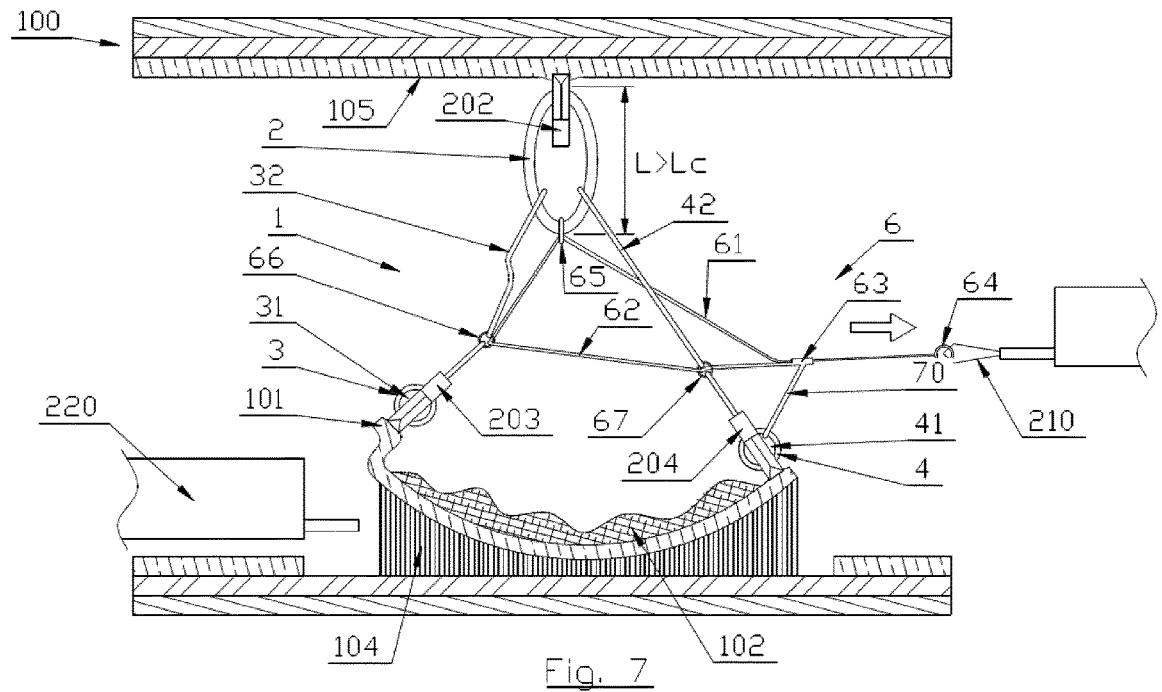
[Fig.8]
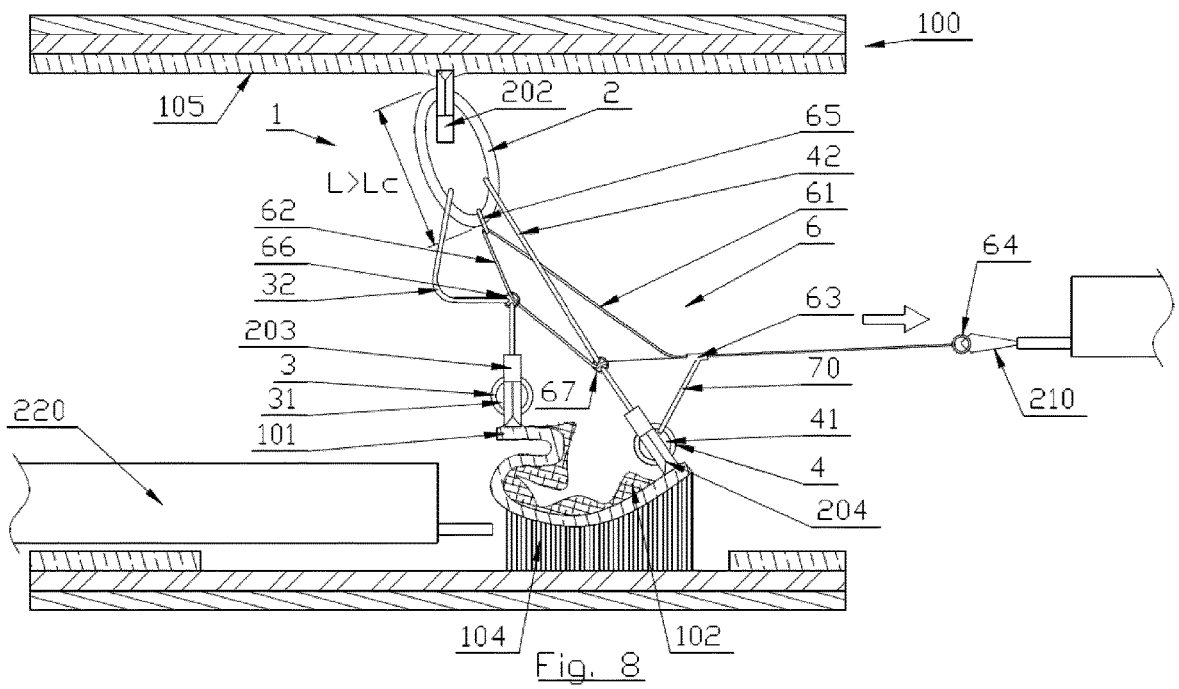

ADJUSTABLE ENDOSCOPIC TRACTION DEVICE

CROSS-REFERENCE TO RELATED APPLICATIONS

The present application claims priority to PCT application serial no. PCT/EP2023/060803 filed Apr. 25, 2023, which claims priority to French patent application serial no. FR2203841, filed Apr. 26, 2022, each herein incorporated by reference in their entireties.

TECHNICAL FIELD OF THE INVENTION

The present invention relates to the technical field of endoscopic devices, and more specifically to traction devices of a biological tissue, for example used for the resection of superficial tumors of the digestive tract.

PREVIOUS STATE OF THE ART

Traction devices are known that are used for the resection of superficial tumors of the digestive tract. Such a traction device generally comprising a proximal anchor and an elastic member configured to exert a proximal traction force onto the proximal anchor.

In practice, the technique that is used to resect a superficial tumor of the digestive tract is the submucosal dissection. It is a complex technique that makes it possible to resect superficial tumors in a minimally invasive way. The submucosal dissection consists in separating the tumoral mucosa from the rest of the wall of the digestive tract, in particular from the muscle, by using the submucosa as a dissection plane. This surgery is said minimally invasive, because it respects the organ with rather short healing times relatively to traditional invasive surgery.

A traction device makes the submucosal dissection easier by moving by traction the mucosa away from the muscle in order to expose the submucosa. To do so, the proximal anchor is fixed to a proximal part of the tumoral mucosa thanks to a an endoscopic hemoclip, and the elastic member is fixed to the opposite wall of the digestive tract in order to exert a traction force on the proximal part of the tumoral mucosa that makes it possible to separate said tumoral mucosa from the rest of the wall of the digestive tract.

However, current traction devices are not fully satisfactory. Indeed, after resecting the first part of the submucosa under the proximal part of the tumoral mucosa, said proximal part relaxes and the traction force exerted by the elastic member onto the proximal anchor becomes insufficient to adequately expose the submucosa. Then, it becomes difficult to insert the dissection device and continue the dissection surgery in good conditions.

In this context, the aim of the invention is to provide a traction device for sufficiently exposing the submucosa so as to provide suitable conditions for the dissection device to move freely throughout the entire resection of the tumor mucosa.

DISCLOSURE OF THE INVENTION

The solution of the invention is a traction device for a biological tissue as defined in the appended claim 1. The invention also relates to the variants of the dependent claims. A person skilled in the art shall understand that each characteristic of the variants of the dependent claims and of the description can be independently combined to the characteristics above without constituting an intermediate generalization.

DESCRIPTION OF THE FIGURES

Other characteristics and advantages of the invention will appear thanks to the following description of particular embodiments of the invention, produced as a guide and non-limitative with a reference to the appended pictures, where:

FIG. 1 shows a schematic view of a first embodiment of the traction device according to the invention;

FIG. 2 shows a schematic view of a second embodiment of the traction device according to the invention;

FIG. 7 shows a schematic view of the embodiment of the traction device of figure [FIG. 1] after adjustment of the proximal length by traction on the end of the body of the clamp and before dissection of the newly exposed submucosa;

FIG. 8 shows a schematic view of the embodiment of the traction device of figure [FIG. 1] after dissection of the proximal part of the exposed submucosa of [FIG. 7] after adjustment of the proximal length by traction on the end of the body of the clamp and before dissection of the rest of the submucosa;

DETAILED DESCRIPTION

Figure 4:
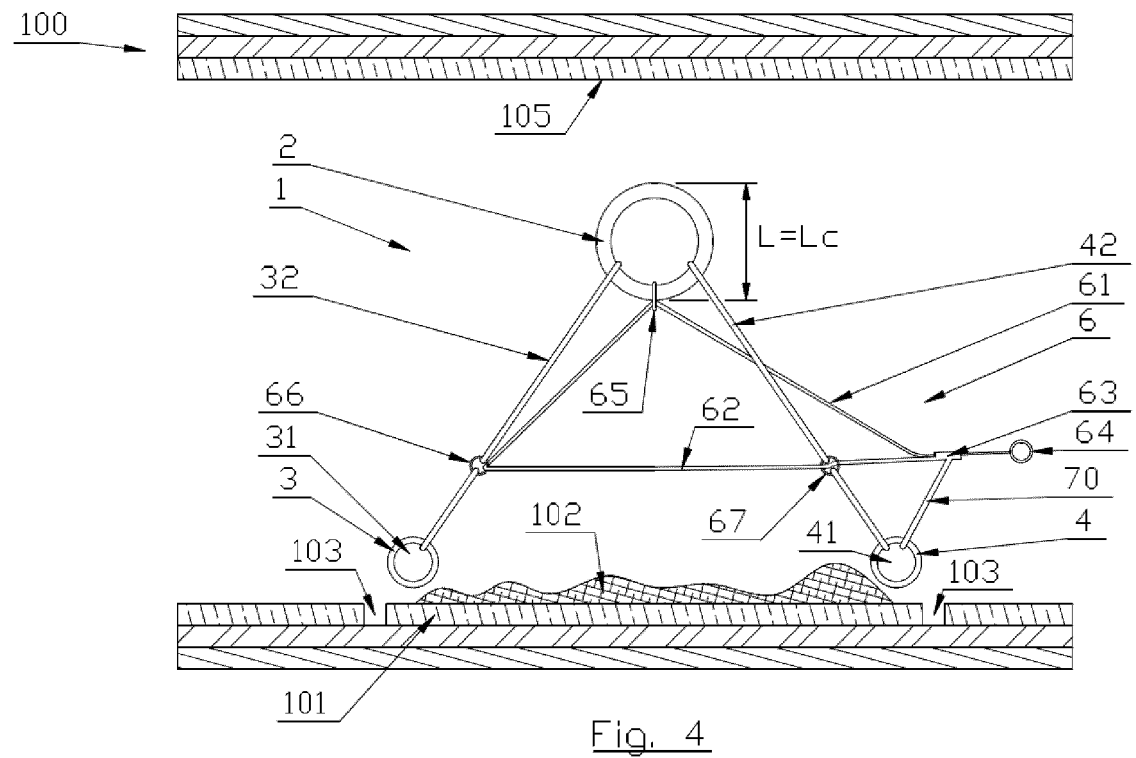
FIG. 4 shows a schematic view of the embodiment of the traction device of figure [FIG. 1] positioned at a biological tissue to resect in a digestive tract.

With reference to figures [FIG. 1] to [FIG. 8], the invention relates to a traction device (1) of a biological tissue (101). In practice, the biological tissue (101) can be a tumor mucosa as pictured in figures [FIG. 4] to [FIG. 8]. The biological tissue is generally located in a cavity of the human body, such as the digestive tract.

The traction device (1) comprises a proximal anchor (3). It can be a round-shaped loop, as in the embodiment of FIG. 1, triangular, rectangular, or any shape suitable for the person skilled in the art. This loop can be rigid, flexible or elastic. For example, the loop can be made of metal, plastic, latex, or any other material suitable for the person skilled in the art. The loop can also be made with a wire made of cotton, silk, polyester, nylon, or any other material suitable for the person skilled in the art. Preferably, the proximal anchor (3) is made of at least one hypoallergenic material such as polyglecaprone, polybutester, glycomer, polyglactin, polyglyconate, polydioxanone, polypropylen. Ingeniously, the proximal anchor (3) features a surface coating made of at least one hypoallergenic material of the type of those describe above. Preferably, the loop that constitutes the proximal anchor (3) features an opening (31) configured to allow a jaw of an endoscopic hemoclip (203) to move freely. In particular, the loop can feature an opening (31) that extends beyond a 8 mm diameter half-circle. As a rule, an endoscopic hemoclip is a clamp with two gripping surfaced jaws. The endoscopic hemoclip is configured to fix to a biological tissue by clamping of said biological tissue between its jaws.

The traction device (1) also comprises a distal anchor (4). It can be a round-shaped loop, as in the embodiment of FIG. 1, triangular, rectangular, or any shape suitable for the person skilled in the art. This loop can be rigid, flexible or elastic. For example, the loop can be made of metal, plastic, latex, or any other material suitable for the person skilled in the art. The loop can also be made with a wire made of cotton, polyester, nylon, or any other material suitable for the person skilled in the art. Preferably, the distal anchor (4) is made of at least one hypoallergenic material such as those described above. Ingeniously, the distal anchor (4) comprises a surface coating made of at least one hypoallergenic material such as those described above. Preferably, the loop that constitutes the distal anchor (4) features an opening (41) configured to allow a jaw of an endoscopic hemoclip (204) to move freely. In particular, the loop can feature an opening (41) that extends beyond a 5 mm diameter half-circle.

The traction device (1) still comprises an elastic member (2). It comprises at least one elastic part with a length (L) and with a Young modulus (E). By "at least one elastic part", it shall be understood that the elastic member (2) can be totally elastic or may comprise at least one elastic part. In the embodiments as pictured in figures [FIG. 1] to [FIG. 8], the elastic part can be made of an elastic material with a Young modulus (E). In practice, the elastic part can be made of an elastomer, for example of rubber, of a thermoplastic elastomer (TPE), of polyethylene terephthalate (PET), etc. Ingeniously, the elastic part is made of latex-based elastomer. Preferably, the elastic part is made of one hypoallergenic material, such as a silicon-based elastomer. When the material of the elastic part features allergic hazard, the elastic part may feature a coating made of a hypoallergenic material with a Young modulus (Er) not more than the Young material (E) and of the type of silicon-based elastomer. The elastic part can have the shape of a ring, like in the embodiments of figures [FIG. 1] to [FIG. 3]. The ring can have a diameter between 3 mm and 10 mm and a section diameter between 0.5 mm and 3 mm. In some embodiments, the elastic part can have the shape of a strip, a cylinder, or any other shape suitable to the person skilled in the art. In other embodiments, the elastic part have the shape of a spring.

The Young modulus (E) is less than 0.1 GPa. Advantageously, the Young modulus (E) is between 0.001 GPa and 0.05 GPa. Preferably, the Young modulus (E) is between 0.008 GPa and 0.03 GPa.

The elastic member (2) can feature an opening configured to allow a jaw of an endoscopic hemoclip (202) to move freely. The passageway can be an opening through the elastic member (2). In some embodiments, the passageway can have the shape of a cylindric or toric insert or any other shape suitable to the person skilled in the art. In particular, the passageway can extend beyond a 5 mm diameter half-circle. When the elastic part of the elastic member (2) is ring-shaped, the opening of the ring can play the role of a passageway.

The elastic part is configured to exert a traction force on the distal anchor (4) and on the proximal anchor (3) when the length (L) is extended beyond a contracted length (Lc).

The proximal anchor (3) is mounted so as to move relative to the elastic member (2) between a minimal proximal distance and a maximal proximal distance. The minimal proximal distance is preferably between 0 mm and 10 mm. The maximal proximal distance is preferably between 10 mm and 50 mm. As in the embodiment pictured in figure [FIG. 1], the proximal anchor (3) can be mounted so as to move relative to the elastic member (2) thanks to of a proximal wire (32). It can be made of cotton, polyester, nylon, or any other material suitable for the person skilled in the art. The proximal wire can have a length between 10 mm and 50 mm. In some embodiments, the proximal anchor (3) can be mounted so as to move relative to the elastic member (2) thanks to a flexible strip or a flexible rod.

The traction device (1) comprises an adjustment member (6). It is configured to adjust the maximal proximal distance between an initial maximal proximal distance and a final maximal proximal distance less than the initial maximal proximal distance.

In a first embodiment of the adjustment member as pictured in figure [FIG. 1], the adjustment member (6) can comprise a clamp (61). The later comprises a body (62) and a cage (63). The body (62) can have a cylindric or parallelepipedon-shaped profile or any other shape of profile suitable for the person skilled in the art. The body (62) has preferably a diameter or a thickness between 0.2 mm and 5 mm. The body (62) can have a length between 5 cm and 20 cm. The cage (63) is so configured that the body (62) can move freely in order to create a closed curve with a circumference of variable length. The body (62) can comprise one or several visual marks, wherein each of said visual marks makes it possible to specify a length with a given circumference when said visual mark is located at the level of the cage (63). In particular, the visual marks can be colored lines along the body (62). In an embodiment, the visual marks can be colored zones along the body (62). Preferably, the clamp (61) comprises between 2 and 6 visual marks. The end of the body (62) opposite to the cage (63) can comprise a drawing loop (64). This drawing loop (64) is preferably configured to allow the seizing by a clamp for endoscopic surgery (210). In particular, the drawing loop (64) can have a diameter between 5 mm and 20 mm. The clamp (61) can be made of a plastic material, a composite material, or any other material suitable for the person skilled in the art. Preferably, the clamp (61) is made of a hypoallergenic material such as those described above. The clamp (61) can ingeniously be made of a shape-memory material such as nitinol.

The clamp (61) can comprise a non-return mechanism configured to prevent the body (62) from sliding in a direction that increases the length of its circumference. The non-return mechanism can be of any kind suitable for the person skilled in the art.

In particular, the non-return mechanism can be flexible non-return bristles or non-return strips located on the body (62) of the clamp (61) in order to:
  move closer to the body (62) when the part of said body, on which said non-return bristles or said non-return strips are fixed, moves in the cage (63) in the direction that reduces the length of the circumference,
  move away from the body (62) and abut the cage (63) when the part of said body, on which said non-return bristles or said non-return strips are fixed, tends to move in said cage in the direction that increases the length of the circumference.

In an embodiment, the anti-return mechanism can be stops located along the body (62) and at least one flexible strip located in the cage (63), wherein said at least one strip is configured to:
move away from the body (62) in order to let pass the stops when said body moves in the cage (63) in the direction that reduces the length of the circumference,
move closer to the body (62) in order to hamper the stops when said body tends to move in the cage (63) in the direction that increases the length of the circumference, In other embodiments, the non-return mechanism comprises toothed elements that move in a cone constituted by the cage (63) so that the toothed elements:
move away from each other so that the body (62) moves freely when it moves in the cage (63) in the direction that reduces the length of the circumference,
move closer to each other in order to exert a pressure onto the body (62) so that said body cannot move freely in said cage (63) when said body tends to move in said cage in the direction that increases the length of the circumference.

Figure 3:
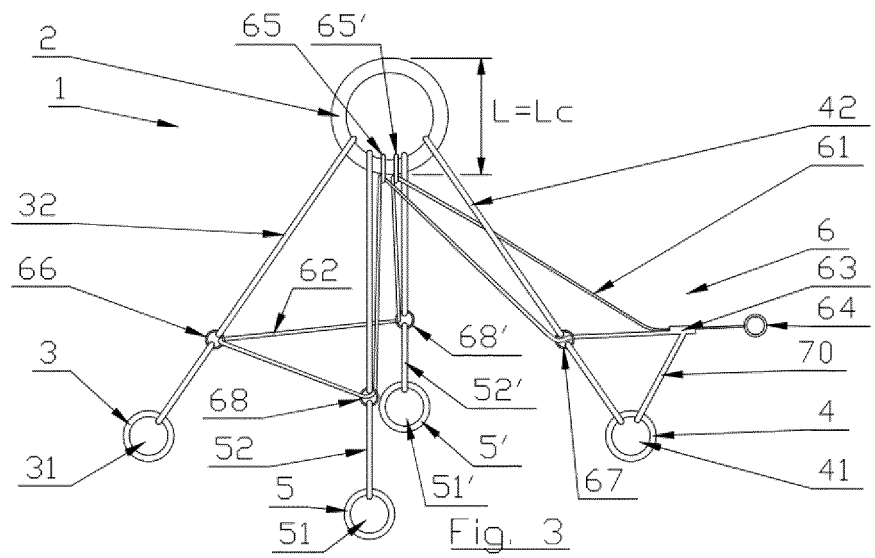
FIG. 3 shows a schematic view of a third embodiment of the traction device according to the invention.

With reference to the embodiments pictures in figures [FIG. 1 to FIG. 3], the adjustment member (6) can also comprise a central guide (65) located on the elastic member (2). The central guide (65) is so configured that the body (62) of the clamp (61) can move freely. Although some embodiments do not comprise a central guide, the presence of a central guide (65) improves the function of adjustment of the adjustment member (6).

As pictured in figures [FIG. 1 to FIG. 3], the central guide (65) can be a ring mounted on the elastic member (2). The central guide (65) can also be an opening through the elastic member (2). In some embodiments, the central guide (65) can have the shape of a cylindric or toric insert or any other shape suitable to the person skilled in the art. The central guide (65) can feature a passageway whose dimensions are at least more than 0.2 mm, preferably more than 0.5 mm at the diameter or the thickness of the body (62) of the clamp (61).

The adjustment member (6) can also comprise a proximal guide (66) configured so that the body (62) of the clamp (61) can move freely. The proximal guide (66) can be located on the proximal anchor (3). The proximal guide (66) can be of any kind suitable for the person skilled in the art.

In particular, when the proximal anchor (3) is made with a wire, the proximal guide (66) can have the shape of a cylindric or toric insert or any other shape suitable to the person skilled in the art.

As well, when the proximal anchor (3) is made of a rigid material, the proximal guide (66) can be made in one piece with the body of said proximal anchor. Then, the proximal guide (66) can have the shape of an opening located on the body of the proximal anchor (3) or of a cylinder, a ring, or any other shape protruding from the body of the proximal anchor (3) toward the inner side or the outer side of said proximal anchor.

In a particular embodiment, the opening (31) of the proximal anchor (3) works as a proximal guide (66).

The proximal guide (66) can alternatively be located on the proximal wire (32). In particular, the proximal guide (66) can be located at the end of the proximal wire (32). The proximal guide (66) can as well be located between two parts of the proximal wire (32), like in the embodiments as pictured in figures [FIG. 1] to [FIG. 8]. The proximal guide (66) is advantageously located close to the proximal anchor (3). The proximal guide (66) can have the shape of a cylindric or toric insert or any other shape suitable to the person skilled in the art. When the proximal anchor (3) is a strip, the proximal guide (66) can have the shape of an eyelet.

The proximal guide (66) can feature a passageway whose dimensions are at least more than 0.2 mm, preferably more than 0.5 mm at the diameter or the thickness of the body (62) of the clamp (61).

In this first embodiment of the adjustment member (6), the clamp (61) is then configured to reduce the maximal proximal distance when the length of its circumference decreases.

In a second not pictured embodiment of the adjustment member (6), it can comprise a proximal coil configured to roll up the proximal wire (32) when the traction force on said proximal wire is less than a return force. The return force is preferably between 0.2 N and 1.8 N. In an embodiment, the proximal coil comprises a drum configured to receive the winding of the proximal wire (32). The proximal coil also comprises a casing, on which the drum is so mounted that it can rotate freely. The proximal coil eventually comprises a return spring configured to initiate the winding of the proximal wire (32) around the drum when the traction force on said proximal wire is less than the return force. The casing can be fixed to the elastic member (2). Ingeniously, in an embodiment, the return spring works as the elastic member (2).

The distal anchor (4) can be mounted so as to move relative to the elastic member (2) between a minimal distal distance and a maximal distal distance. The minimal distal distance is preferably between 0 mm and 10 mm. The maximal distal distance is preferably between 10 mm and 50 mm. In a preferential embodiment of the distal anchor (4), the maximal distal distance is not more than ⅓ of the maximal proximal distance. As in the embodiment pictured in figures [FIG. 1] to [FIG. 8], the distal anchor (4) can be mounted so as to move relative to the elastic member (2) thanks to a distal wire (42). It can be made of cotton, polyester, nylon, or any other material suitable for the person skilled in the art. The distal wire (42) can have a length between 10 mm and 50 mm. In some embodiments, the distal anchor (4) can be mounted so as to move relative to the elastic member (2) thanks to a flexible strip or a flexible rod.

The adjustment member (6) can then be configured to adjust the maximal distal distance between an initial maximal distal distance and a final maximal distal distance less than the initial maximal distal distance.

According to the first embodiment of the adjustment member (6), it can comprise a distal guide (67) configured so that the body (62) of the clamp (61) can move freely. The distal guide (67) can be located on the distal anchor (4).

The distal guide (67) can be of any kind suitable for the person skilled in the art.

In particular, when the distal anchor (4) is made with a wire, the distal guide (67) can have the shape of a cylindric or toric insert or any other shape suitable to the person skilled in the art.

As well, when the distal anchor (4) is made of a rigid material, the distal guide (67) can be made in one piece with the body of said distal anchor. Then, the distal guide (67) can have the shape of an opening located on the body of the distal anchor (4) or of a cylinder, a ring, or any other shape protruding from the body of the distal anchor (4) toward the inner side or the outer side of said distal anchor.

In a particular embodiment, the opening (41) of the distal anchor (4) works as a distal guide (67).

The distal guide (67) can alternatively be located on the distal wire (42). In particular, the distal guide (67) can be located at the end of the distal wire (42). The distal guide (67) can as well be located between two parts of the distal wire (42), like in the embodiments as pictured in figures [FIG. 1] to [FIG. 8]. In this case, the distal guide (67) is advantageously located close to the distal anchor (4). The distal guide (67) can have the shape of a cylindric or toric insert or any other shape suitable to the person skilled in the art. When the distal anchor (4) is a strip, the distal guide (67) can have the shape of an eyelet.

The distal guide (67) can feature a passageway whose dimensions are at least more than 0.2 mm, preferably more than 0.5 mm at the diameter or the thickness of the body (62) of the clamp (61).

In this first embodiment of the adjustment member (6), the clamp (61) can be configured to reduce the maximal distal distance when the length of its circumference decreases.

In a second not pictured embodiment of the adjustment member (6), it can comprise a distal coil configured to roll up the distal wire (42) when the traction force on said distal wire is less than a return force. The return force is preferably between 0.2 N and 1.8 N. In an embodiment, the distal coil comprises a drum configured to receive the winding of the distal wire (42). The distal coil also comprises a casing, on which the drum is so mounted that it can rotate freely. The distal coil eventually comprises a return spring configured to initiate the winding of the distal wire (42) around the drum when the traction force on said distal wire is less than the return force. The casing can be fixed to the elastic member (2). Ingeniously, in an embodiment, the return spring works as the elastic member (2). The elastic member (2) comprises then several elastic items, i.e. a return spring for the proximal coil and a return spring for the distal coil. Ingeniously, the casing of the proximal coil and the casing of the distal coil constitute a single casing.

The proximal anchor (3) can be mounted so as to move relative to the elastic member (4) between a minimal spacing distance and a maximal spacing distance. The minimal spacing distance is preferably between 0 mm and 10 mm. The maximal spacing distance is preferably between 10 mm and 50 mm. In practice, all the embodiments described above for the distal anchor (4) and the proximal anchor (3) allow the proximal anchor (3) to move relative to the distal anchor (4).

The adjustment member (6) can then be configured to reduce the maximal spacing distance between an initial maximal spacing distance and a final maximal spacing distance less than the initial maximal spacing distance. In practice, all the embodiments described above for the adjustment member (6) make it possible to reduce the maximal spacing distance.

Figure 10:
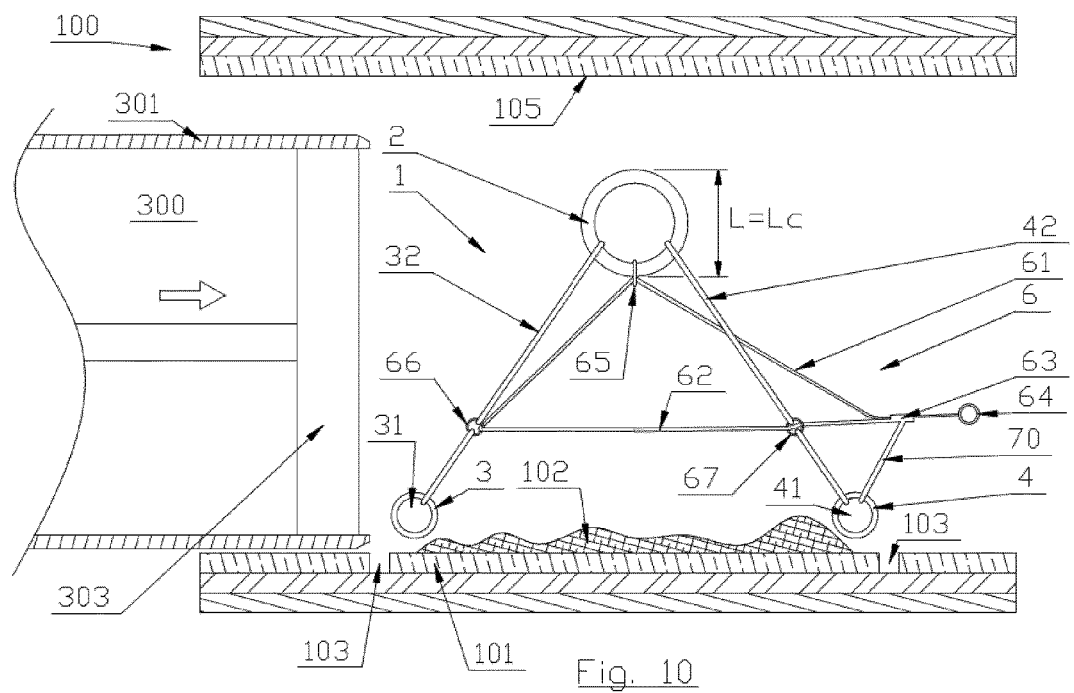
FIG. 10 shows a schematic view of the embodiment of the traction device of figure [FIG. 1] outside the releasing device after releasing on the surgery zone.

As pictured in figures [FIG. 1] to [FIG. 10], the adjustment member (6) can comprise a cable tie (70) configured to keep the cage (63) at a specified tightening distance from the distal anchor (4). The tightening distance is preferably between 0 mm and 20 mm. The tightening distance is preferably less than 5 mm. This cable tie (70) can be a wire between the cage (63) of the clamp (61) to the distal anchor (4). The wire can be made of cotton, polyester, nylon, or any other material suitable for the person skilled in the art. Alternatively, the cable tie (70) can be a strip, a rod, a ring or any other mechanical link suitable for the person skilled in the art. The cable tie (70) can then be made of tissue, plastic, metal, or any other material suitable for the person skilled in the art. Preferably, the material of the cable tie (70) is hypoallergenic. If it is not, said cable tie (70) features a hypoallergenic coating.

In a variant of embodiment at the cable tie, the adjustment member (6) can also comprise a tightening guide configured so that the body (62) of the clamp (61) can move freely, so that the cage (63) of said clamp is stuck between the distal guide (67) and said tightening guide.

The tightening guide can be located on the distal anchor (4). The tightening guide can be of any kind suitable for the person skilled in the art.

In particular, when the distal anchor (4) is made with a wire, the tightening guide can have the shape of a cylindric or toric insert or any other shape suitable to the person skilled in the art.

As well, when the distal anchor (4) is made of a rigid material, the tightening guide can be made in one piece with the body of said distal anchor. Then, the tightening guide can have the shape of an opening located on the body of the distal anchor (4) or of a cylinder, a ring, or any other shape protruding from the body of the distal anchor (4) toward the inner side or the outer side of said distal anchor.

The tightening guide can alternatively be located on the distal wire (42). In this case, the tightening guide is advantageously located close to the distal anchor (4). The tightening guide can have the shape of a cylindric or toric insert or any other shape suitable to the person skilled in the art. When the distal anchor (4) is a strip, the tightening guide can have the shape of an eyelet.

The tightening guide can also be located on a tightening wire. It is fixed to the distal anchor (4). The tightening wire can be made of cotton, polyester, nylon, or any other material suitable for the person skilled in the art. The tightening wire can have a length between 5 mm and 20 mm. In some variants of embodiment, the tightening wire is replaced by a flexible strip or a flexible rod. The tightening guide is advantageously located close to the distal anchor (4). The tightening guide can have the shape of a cylindric or toric insert or any other shape suitable to the person skilled in the art.

The tightening guide can feature a passageway whose dimensions are at least more than 0.2 mm, preferably more than 0.5 mm at the diameter or the thickness of the body (62) of the clamp (61).

As in the embodiment pictured in figure [FIG. 2], the traction device (1) can comprise a second proximal anchor (3') of the same type as the proximal anchor (3) described above. This means that the second proximal anchor (3') has the same characteristics as the proximal anchor (3) described above, in particular in terms of shape, material, mobility, distance to the other items, etc. In particular, the second proximal anchor (3') can comprise an opening (31') and be mounted so that it can move freely relative to the elastic member thanks to a second proximal wire (32'). As previously described, the elastic part of the elastic member (2) is configured to exert a traction force on the second proximal anchor (3') when its length (L) is extended beyond the contracted length (Lc). Furthermore, the second proximal anchor (3') can be mounted so as to move relative to the previously described proximal anchor (3) between a minimal frontal distance and a maximal frontal distance.

Similarly, the adjustment member (6) can be configured to adjust the second maximal proximal distance between a second initial maximal proximal distance and a second final maximal proximal distance less than the second initial maximal proximal distance. For this reason, the adjustment member (6) can comprise a second proximal guide (66') or a second proximal coil according to the selected embodiment. The adjustment member (6) can also be configured to adjust the maximal frontal distance between an initial maximal frontal distance and a final maximal frontal distance less than the initial maximal frontal distance.

With reference to the embodiment pictured in figure [FIG. 2], the adjustment member (6) can also comprise a second central guide (65') located on the elastic member (2). The second central guide (65') is of the same type as the central guide (65). This means that the second central guide (65') has the same characteristics as the central guide (65), in particular in terms of shape, material, location relative to the elastic member (2), etc. For this reason, the second central guide (65') is so configured that the body (62) of the clamp (61) can move freely. Advantageously, the body (62) of the clamp (61) moves through the distal guide (67), then through the central guide (65), then through the proximal guide (66), then through the second proximal guide (66'), then through the second central guide (65'). Alternatively, and as pictured in figure [FIG. 2], the body (62) of the clamp (61) moves through the distal guide (67), then through the second central guide (65'), then through the second proximal guide (66'), then through the proximal guide (66), then through the central guide (65).

As in the embodiment pictured in figure [FIG. 3], the traction device (1) can further comprise one or several lateral anchors (5, 5'). Preferably, the traction device (1) comprises an even number of lateral anchors (5, 5'). For each pair of lateral anchors (5, 5'), one of the lateral anchors (5, 5') is located on one side of the traction device (1), while the other of the lateral anchors is located on the other side of said traction device.

A lateral anchor (5, 5') can be a round-shaped loop, triangular, rectangular, or any shape suitable for the person skilled in the art. This loop can be rigid, flexible or elastic. For example, the loop can be made of metal, plastic, latex, or any other material suitable for the person skilled in the art. The loop can also be made with a wire made of cotton, polyester, nylon, or any other material suitable for the person skilled in the art. Preferably, the lateral anchor (5, 5') is made of at least one hypoallergenic material such as those described above. Ingeniously, the lateral anchor (5, 5') comprises a hypoallergenic coating made of at least one hypoallergenic material as described above. Preferably, the loop features an opening (51, 51') configured to allow a jaw of an endoscopic hemoclip to move freely. In particular, the loop can feature an opening (51, 51') that extends beyond a 8 mm diameter half-circle.

The elastic part of the elastic member (2) can then be configured to exert a traction force on the lateral anchors (5, 5') when its length (L) is extended beyond the contracted length (Lc).

The lateral anchor (5, 5') can be mounted so as to move relative to the elastic member (2) between a minimal lateral distance and a maximal lateral distance. The minimal lateral distance is preferably between 0 mm and 10 mm. The maximal lateral distance is preferably between 10 mm and 50 mm. The lateral anchor (5, 5') can be mounted so as to move relative to the elastic member (2) thanks to a lateral wire (52, 52'). It can be made of cotton, polyester, nylon, or any other material suitable for the person skilled in the art. The lateral wire (52, 52') can have a length between 10 mm and 50 mm. In some variants of embodiment, the lateral anchor (5, 5') can be mounted so as to move relative to the elastic member (2) thanks to a flexible strip or a flexible rod.

The adjustment member (6) can be configured to adjust the maximal lateral distance between an initial maximal lateral distance and a final maximal lateral distance less than the initial maximal lateral distance.

In its first embodiment, the adjustment member (6) can then comprise, for each lateral anchor (5, 5'), a lateral guide (68, 68') configured so that the body (62) of the clamp (61) can move freely. The lateral guide (68, 68') can be located on the lateral anchor (5, 5'). The lateral guide can be of any kind suitable for the person skilled in the art.

In particular, when the lateral anchor (5, 5') is made with a wire, the lateral guide (68, 68') can have the shape of a cylindric or toric insert or any other shape suitable to the person skilled in the art.

As well, when the lateral anchor (5, 5') is made of a rigid material, the lateral guide (68, 68') can be made in one piece with the body of said lateral anchor. Then, the lateral guide (68, 68') can have the shape of an opening located on the body of the lateral anchor (5, 5') or of a cylinder, a ring, or any other shape protruding from the body of the lateral anchor (5, 5') toward the inner side or the outer side of said lateral anchor.

In a particular embodiment, the opening (51, 51') of the lateral anchor (5, 5') works as a lateral guide (68, 68').

The lateral guide (68, 68') can alternatively be located on the lateral wire (52, 52'). In particular, the lateral guide (68, 68') can be located at the end of the lateral wire (52, 52'). The lateral guide (68, 68') can as well be located between two parts of the lateral wire (52, 52'), like in the embodiment as pictured in figure [FIG. 3]. In this case, the lateral guide (68, 68') is advantageously located close to the lateral anchor (5, 5'). The lateral guide (68, 68') can have the shape of a cylindric or toric insert or any other shape suitable to the person skilled in the art. When the lateral anchor (5, 5') is a strip, the lateral guide (68, 68') can have the shape of an eyelet.

The lateral guide (68, 68') can feature a passageway whose dimensions are at least more than 0.2 mm, preferably more than 0.5 mm at the diameter or the thickness of the body (62) of the clamp (61).

With reference to the embodiments pictured in figure [FIG. 3], the adjustment member (6) can also comprise a second central guide (65') located on the elastic member (2). The second central guide (65') is of the same type as the central guide (65). This means that the second central guide (65') has the same characteristics as the central guide (65) described above, in particular in terms of shape, material, location relative to the elastic member (2), etc. For this reason, the second central guide (65') is so configured that the body (62) of the clamp (61) can move freely. Advantageously, and as pictured in figure [FIG. 3], the body (62) of the clamp (61) moves through the distal guide (67), then through the central guide (65), then through the first lateral guide (68), the through the proximal guide (66), then through the second lateral guide (68'), then through the second central guide (65'). Alternatively, the body (62) of the clamp (61) moves through the distal guide (67), then through the second central guide (65'), then through the second lateral guide (66'), then through the proximal guide (66), then through the first lateral guide (66), then through the central guide (65).

In this first embodiment of the adjustment member (6), the clamp (61) is then configured to reduce the maximal lateral distance when the length of its circumference decreases.

In the second embodiment of the adjustment member (6), it can comprise a lateral coil configured to roll up the lateral wire (52, 52') when the traction force on said lateral wire is less than a return force. The return force is preferably between 0.2 N and 1.8 N. In an embodiment, the lateral coil comprises a drum configured to receive the winding of the lateral wire (52, 52'). The lateral coil also comprises a casing, on which the drum is so mounted that it can rotate freely. The lateral coil eventually comprises a return spring configured to initiate the winding of the lateral wire (52, 52') around the drum when the traction force on said lateral wire is less than the return force. The casing can be fixed to the elastic member (2). Ingeniously, in an embodiment, the return spring works as the elastic member (2). The elastic member comprises then several elastic items, i.e. a return spring for the proximal coil, a return spring for the distal coil and a return spring for the lateral coil. Ingeniously, the casing of the proximal coil, the casing of the distal coil and the casing of the lateral coil constitute a single casing.

The lateral anchor (5, 5') can be mounted so as to move relative to the distal anchor (4) and/or the proximal anchor (3) between a minimal lateral spacing distance and a maximal lateral spacing distance. The minimal lateral spacing distance is preferably between 0 mm and 10 mm. The maximal lateral spacing distance is preferably between 10 mm and 50 mm. In practice, all the embodiments described above for the distal anchor (4), the proximal anchor (3) and the lateral anchors (5, 5') allow the anchors to move relative to each other.

The adjustment member (6) can then be configured to reduce the maximal spacing distance between an initial maximal lateral spacing distance and a final maximal lateral spacing distance less than the initial maximal lateral spacing distance. In practice, all the embodiments described above for the adjustment member (6) make it possible to reduce the maximal lateral spacing distance.

Another aspect of the invention relates to a process of traction of a biological tissue (101) in a cavity thanks to the traction device (1) according to the invention. The process generally takes part in the context of a resection surgery of the mucosa-type biological tissue (101) and featuring a tumor (102). The biological tissue (101) is generally located in the wall of the digestive tract (100). During this procedure, the border of the biological tissue (101) to resect are cut off thanks to an endoscopic dissection device. The figure [FIG. 4] shows the biological tissue (101) after its border (103) has been cut off. The biological tissue (101) must then be separated from the rest of the wall of the digestive tract (100). To do so, it is necessary to apply a traction force onto the biological tissue (101) in order to remove it from the rest of the wall of the digestive tract (100). The submucosa (104), which is made of fibers, shall extend and get exposed, so that it is possible to dissect it with an endoscopic dissection device (220). The traction process makes it possible to exert the traction force onto the biological tissue (101). The traction process comprises the following steps:
a) Fixing the proximal anchor (3) to a proximal part of the biological tissue (101) thanks to a first endoscopic hemoclip (203),
b) Fixing the distal anchor (4) to a distal part of the biological tissue (101) thanks to a second endoscopic hemoclip (204),
c) Fixing the elastic member (2) to a wall (105) of the cavity in front of the biological tissue (101) thanks to a third endoscopic hemoclip (202) so that the elastic part of the elastic member (2) extends beyond the contracted length (Lc) and exerts a traction force onto the distal anchor (4) and onto the proximal anchor (3).

When the biological tissue (101) features a proximal zone more than 3 cm wide, this traction process can also comprise the following step:

d) Fixing the second proximal anchor (3') away from the proximal anchor (3) that was fixed at step a) to the proximal part of the biological tissue (101) thanks to another endoscopic hemoclip.

When the biological tissue (101) extends over more than 8 cm of length and 5 cm of width, this traction process can still comprise at least once the following step according to the number of lateral anchors in the traction device:

e) Fixing a lateral anchor (5, 5') to a lateral part of the biological tissue (101) thanks to another endoscopic hemoclip.

Figure 5:
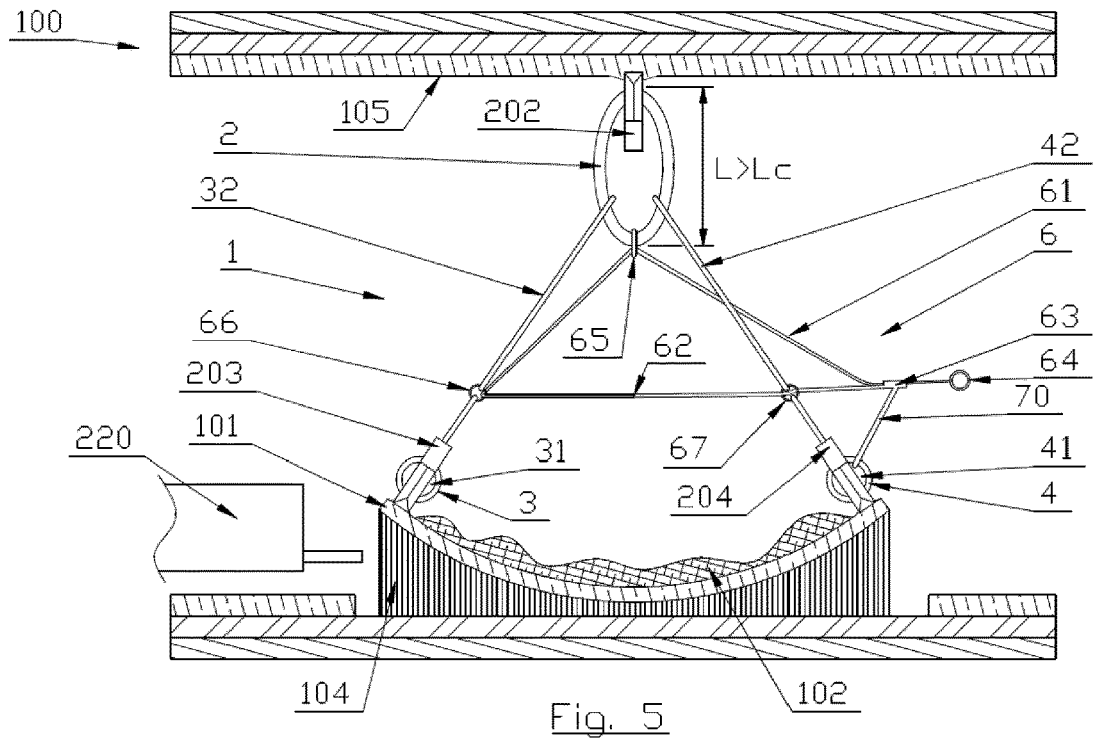
FIG. 5 shows a schematic view of the embodiment of the traction device of figure [FIG. 1] after fixing anchors on the biological tissue and fixing the elastic member onto the digestive tract opposite to the biological tissue and before dissection of the proximal part of the submucosa thanks to the endoscopic dissection device.
Figure 6:
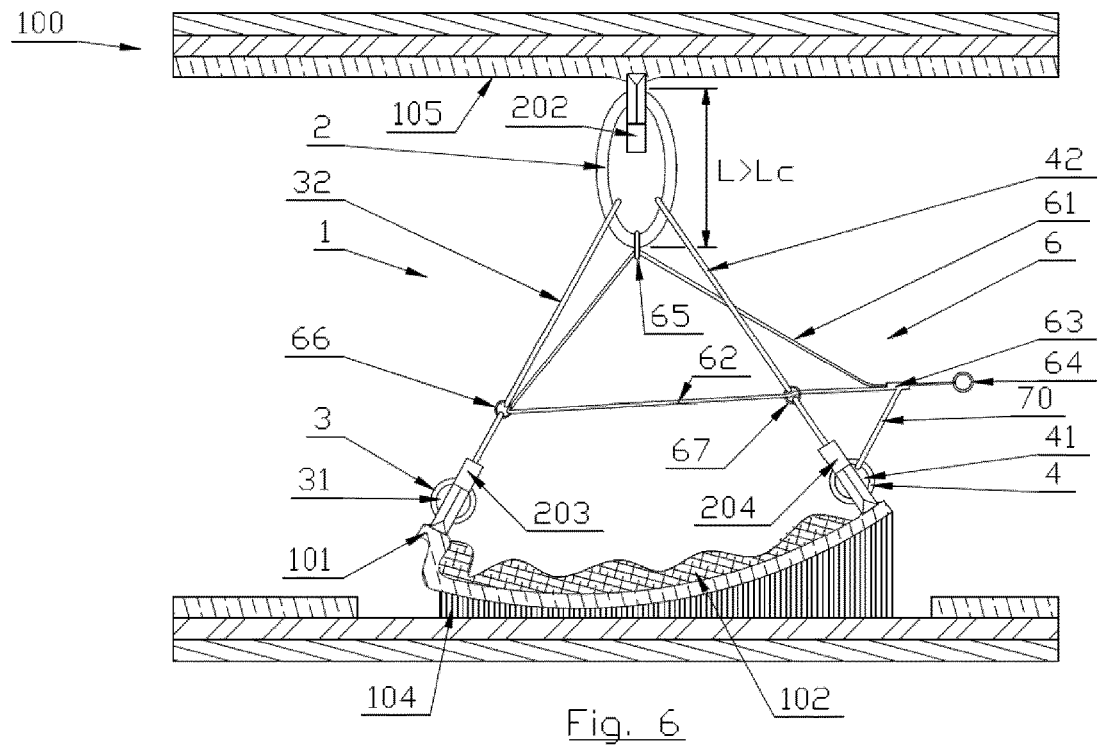
FIG. 6 shows a schematic view of the embodiment of the traction device of figure [FIG. 1] after dissection of the proximal part of the exposed submucosa of [FIG. 5]

Once the first steps of the traction process implemented, as pictured in figure [FIG. 5], the submucosa (104) of the biological tissue (101) is exposed enough. The proximal part of the submucosa (104) is then dissected thanks to the dissection device (220). However, as pictured in figure [FIG. 6], once the proximal part of the submucosa (104) dissected, the proximal part of the biological tissue (101) is no more constrained by the submucosa (104) and relaxes, so that the traction force exerted on said biological tissue is no more enough to expose said submucosa and allow the dissection device (220) to pass.

To solve this problem, the traction process also comprises the following step:
d) Reducing the maximal proximal distance thanks to the adjustment member (6) when the traction force exerted on the proximal anchor (3) falls under a threshold value (Ts).

According to an embodiment selected for the traction device (1), the process can also comprise the following steps, independently or in combination:
e) Reducing the maximal distal distance thanks to the adjustment member (6) when the traction force exerted on the distal anchor (4) falls under a threshold value (Ts),
f) Reducing the second maximal proximal distance thanks to the adjustment member (6) when the traction force exerted on the second proximal anchor (3') falls under a threshold value (Ts).
g) Reducing the maximal lateral distance thanks to the adjustment member (6) when the traction force exerted on the lateral anchor (5, 5') falls under a threshold value (Ts),
e) Reducing the maximal spacing distance thanks to the adjustment member (6) when the traction force exerted on the proximal anchor (3) and/or on the distal anchor (4) falls under a threshold value (Ts),
f) Reducing the maximal spacing distance thanks to the adjustment member (6) when the traction force exerted on the proximal anchor (3) and/or on the distal anchor (4) and/or on one of the lateral anchors (5, 5') falls under a threshold value (Ts), In practice, the threshold (Ts) is where it is no more possible for the dissection device (220) to move without touching the biological tissue (101). The threshold value (Ts) is generally between 0.2 N and 1.8 N.

With reference to figure [FIG. 7], the maximal proximal distance is reduced by the traction onto the body (62) of the clamp (61), so that the length of the circumference of said clamp is reduced. The traction is made thanks to a clamp for endoscopic surgery (210).

Thus, as pictured in figure [FIG. 7], once the maximal proximal distance is reduced, the traction force exerted on the biological tissue (101) is enough again to expose the submucosa (104) and allow the dissection device (220) to pass. The exposed part of the submucosa (104) is then dissected. As previously, after dissection, the biological tissue (101) relaxes and the traction force is no more enough to pursue the dissection. The step d) is then repeated as many times as required, as stipulated on figure [FIG. 8].

Another aspect of the invention relates to a releasing device (300) for the traction device (1) of the invention. The releasing device (300) ingeniously makes it possible to lay the traction device (1) on the biological tissue (101) to pull while preventing the risks of interference with the wall of the digestive tract (100), thus preventing the risks of entanglement of the various movable anchors.

Figure 9:
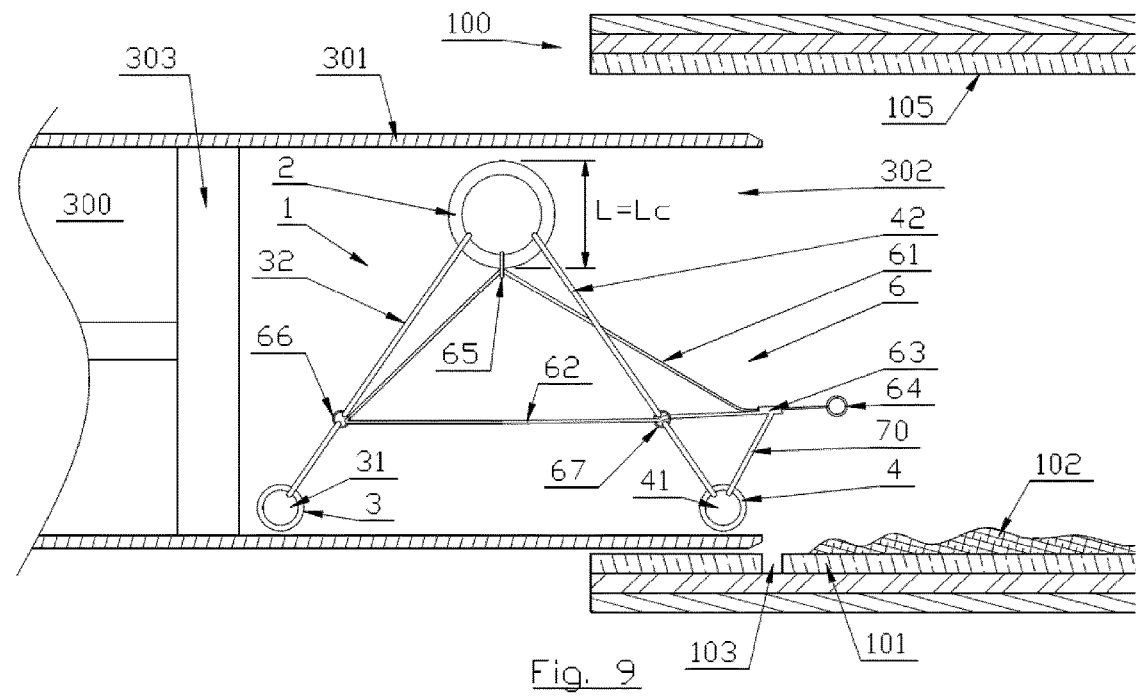
FIG. 9 shows a schematic view of the embodiment of the traction device of figure [FIG. 1] inside the releasing device before releasing on the surgery zone.

With reference to figures [FIG. 9] and [FIG. 10], the releasing device (300) comprises a tube (301). This tube comprises an internal space (302) configured to receive the traction device (1). The tube (301) can comprise a round, rectangular, hexagonal or any other profile section. The diameter, the length or the width of the section can be between 30 mm and 70 mm. The tube (301) can be made of plastic, metal, or any other material suitable for the person skilled in the art.

The releasing device (300) also comprises a piston (303) configured to slide through the inside of the tube (301) to push the traction device (1) out of said tube, as pictured in figure [FIG. 10]. This piston (303) can be operated mechanically or by differential pressure. The piston (303) can be made of plastic, metal, or any other material suitable for the person skilled in the art.

The invention claimed is:

1. A traction device (1) for a biological tissue comprising:
   A proximal anchor (3),
   A distal anchor (4),
   An elastic member (2) comprising at least an elastic part with a length (L) and a Young modulus (E) less than 0.1 GPa, said elastic member being configured to exert a traction force on the distal anchor (4) and on the proximal anchor (3) when said length (L) is extended beyond a contracted length (Lc),
   characterized in that the proximal length (3) is mounted so as to move relative to the elastic member (2) between a minimal proximal distance and a maximal proximal distance, and in that said traction device comprises an adjustment member (6) configured to adjust the maximal proximal distance between an initial maximal proximal distance and a final maximal proximal distance less than the initial maximal proximal distance.

2. A traction device according to claim 1, characterized in that the distal anchor (4) is mounted so as to move relative to the elastic member (2) between a minimal distal distance and a maximal distal distance, and in that the adjustment member (6) is configured to adjust the maximal distal distance between an initial maximal distal distance and a final maximal distal distance less than the initial maximal distal distance.

3. A traction device according to claim 1, characterized in that the proximal anchor (3) is mounted so as to move relative to the distal anchor (4) between a minimal spacing distance and a maximal spacing distance, and in that the adjustment member (6) is configured to reduce the maximal spacing distance between an initial maximal spacing distance and a final maximal spacing distance less than the initial maximal spacing distance.

4. A traction device according to claim 1, characterized in that the elastic part of the elastic member (2) has a Young modulus between 0.001 GPa and 0.05 GPa.

5. A traction device according to claim 1, characterized in that the proximal anchor (3) is mounted so as to move relative to the elastic member (2) thanks to a proximal wire (32).

6. A traction device according to claim 5, characterized in that the adjustment member (6) comprises:
   A clamp (61) comprising a body (62) and a cage (63) so configured that said body can move freely in order to create a closed curve with a circumference of variable length,
   A central guide (65) put together on the elastic member (2) and so configured that the body (62) of the clamp (61) can move freely,
   A proximal guide (66) put together on the proximal anchor (3) or on the proximal wire (32) and so configured that the body (62) of the clamp (61) can move freely,
   The clamp (61) being configured to reduce the maximal proximal distance when the length of its circumference decreases.

7. A traction device according to claim 1, characterized in that the distal anchor (4) is mounted so as to move relative to the elastic member (2) thanks to a distal wire (42).

8. A traction device according to claim 7, characterized in that the adjustment member (6) comprises a distal guide (67) put together on the distal anchor (4) or on the distal wire (42) and so configured that the body (62) of the clamp (61) can move freely, the clamp being configured to reduce the maximal distal distance when the length of its circumference decreases.

9. A traction device according to claim 8, characterized in that the adjustment member (6) comprises a cable tie (70) configured to keep the cage (63) at a given tightening distance from the distal anchor (4).

10. A traction device according to claim 6, characterized in that the clamp (61) comprises a non-return mechanism configured to prevent the body (62) from sliding in a direction that increases the length of its circumference.

* * * * *